(12) United States Patent
Chen et al.

(10) Patent No.: US 11,369,333 B2
(45) Date of Patent: Jun. 28, 2022

(54) METHOD AND APPARATUS FOR DETECTING DOSE DISTRIBUTION OF ARTICLE

(71) Applicants: Tsinghua University, Beijing (CN); Nuctech Company Limited, Beijing (CN); Nucway Company Limited, Beijing (CN)

(72) Inventors: Zhiqiang Chen, Beijing (CN); Yuanjing Li, Beijing (CN); Zhiwei Han, Beijing (CN); Guang Yang, Beijing (CN); Huaili Qin, Beijing (CN); Wenyuan Qi, Beijing (CN); Shan Kuang, Beijing (CN); Aifeng Liang, Beijing (CN); Yanqin Liu, Beijing (CN)

(73) Assignees: Nuctech Company Limited, Beijing (CN); Nucway Company Limited, Beijing (CN); Tsinghua University, Beijing (CN)

( * ) Notice: Subject to any disclaimer, the term of this patent is extended or adjusted under 35 U.S.C. 154(b) by 225 days.

(21) Appl. No.: 16/946,508

(22) Filed: Jun. 24, 2020

(65) Prior Publication Data
US 2020/0405255 A1    Dec. 31, 2020

(30) Foreign Application Priority Data

Jun. 27, 2019 (CN) .......................... 201910566051.3
Jun. 27, 2019 (CN) .......................... 201910568018.4

(51) Int. Cl.
*A61B 6/00* (2006.01)
*A61B 6/02* (2006.01)

(52) U.S. Cl.
CPC .............. *A61B 6/542* (2013.01); *A61B 6/022* (2013.01); *A61B 6/461* (2013.01); *A61B 6/487* (2013.01); *A61B 6/5205* (2013.01); *A61B 6/5288* (2013.01)

(58) Field of Classification Search
CPC ...... A61L 2/082; A61L 2/087; A61L 2202/24; A61B 6/03; A61B 6/032; A61B 6/463;
(Continued)

(56) References Cited

U.S. PATENT DOCUMENTS

| | | | |
|---|---|---|---|
| 6,396,065 B1 * | 5/2002 | Kimura | A61L 2/087 250/455.11 |
| 2003/0016782 A1 | 1/2003 | Kaufman et al. | |
| 2006/0081788 A1 | 4/2006 | Hoernig | |

FOREIGN PATENT DOCUMENTS

| | | |
|---|---|---|
| CN | 1995993 A | 7/2007 |
| CN | 100998497 A | 7/2007 |

(Continued)

OTHER PUBLICATIONS

"Chinese Application No. 201910568018.4, First Office Action dated Apr. 14, 2021", (Apr. 14, 2021), 11 pgs. [partial translation].
(Continued)

*Primary Examiner* — David E Smith
*Assistant Examiner* — Hsien C Tsai
(74) *Attorney, Agent, or Firm* — Schwegman Lundberg & Woessner, P.A.

(57) ABSTRACT

The present disclosure provides a method and apparatus for detecting a dose distribution of an article. The method includes performing a fluoroscopy scanning on the article to be detected, to obtain mass data per unit area or unit volume for each point of the article to be detected; obtaining corresponding dose distribution data based on the mass data per unit area or unit volume and a preset mapping model,
(Continued)

wherein the preset mapping model includes a mapping relationship between mass per unit area or unit volume and the dose distribution of the article under irradiation of a preset amount of energy; and matching the dose distribution data with a fluoroscopy image of the article to be detected, to generate and display a radiation image.

19 Claims, 11 Drawing Sheets

(58) Field of Classification Search
CPC ......... A61B 6/469; A61B 6/467; A61B 6/503; A61B 6/5288
See application file for complete search history.

(56) References Cited

FOREIGN PATENT DOCUMENTS

| | | |
|---|---|---|
| CN | 101937729 A | 1/2011 |
| CN | 102023306 A | 4/2011 |
| CN | 102540233 A | 7/2012 |
| CN | 105403581 A | 3/2016 |
| CN | 106772528 A | 5/2017 |
| CN | 108169256 A | 6/2018 |
| CN | 108508052 A | 9/2018 |
| JP | H0866388 A | 3/1996 |
| JP | 2001025501 A | 1/2001 |
| WO | WO-2018158380 A1 | 9/2018 |

OTHER PUBLICATIONS

"International Application No. PCT/CN2020/096606, International Search Report and Written Opinion dated Sep. 1, 2020", (Sep. 1, 2020), 10 pgs.

Qin, Huaili, et al., "Concept development of X-ray mass thickness detection for irradiated items upon electron beam irradiation processing", Radiation Physics and Chemistry143 (2018) 8-13, (Sep. 14, 2017), 8-13.

\* cited by examiner

METHOD AND APPARATUS FOR DETECTING DOSE DISTRIBUTION OF ARTICLE

CROSS-REFERENCE TO RELATED APPLICATION

This application is based upon and claims priority to Chinese Patent Application No. 201910568018.4, titled "RADIATION IMAGING METHOD AND APPARATUS BASED ON DETECTION OF DOSE FIELD" and filed on Jun. 27, 2019 and Chinese Patent Application No. 201910566051.3, titled "METHOD AND APPARATUS FOR DETECTING SPATIAL DOSE DISTRIBUTION OF ARTICLE" and filed on Jun. 27, 2019, the entire content of which is incorporated herein by reference.

TECHNICAL FIELD

The present disclosure relates to the technical field of irradiation processing, and in particular to a method and apparatus for detecting a dose distribution of an article.

BACKGROUND

Irradiation processing is to use physical, chemical and biological effects of rays on substances to achieve a predetermined target effect. Irradiation processing may be used for food preservation, sterilization of medical and health care products, sterilization of packaging materials, sterilization of cosmetics, and modification of materials. Irradiation processing involves a wide range of fields, is an important processing stage in industries such as food processing, medical and pharmaceutical products processing, which are related to the national economy and the people's livelihood, and has become an important component of the national economy.

When an electron beam is used for irradiation processing, due to limited penetration of the electron beam, for a cargo with considerable thickness, a distribution of a dose field inside the cargo is particularly important. Once a package size and a loading method of the cargo do not match a penetration ability of the electron beam, it is easy to have accidents of irradiating quality, such as impenetrability or failure to meet a standard dose field. Therefore, the real dose distribution in the cargo is critical to irradiation process, production plan, and quality control.

Therefore, before the irradiation processing, it may be necessary to know dose distribution data of the cargo. At present, a commonly used detection method is to unpack the cargo and bury a dosimeter in the cargo for testing, which involves low efficiency, high cost and high technical requirements.

SUMMARY

The embodiments of the present disclosure provide a method and apparatus for detecting a dose distribution of an article.

In an aspect, an embodiment of the present disclosure provides a method for detecting a dose distribution of an article. The method includes performing a fluoroscopy scanning on the article, to obtain mass data per unit area or unit volume for each point of the article; obtaining corresponding dose distribution data based on the mass data per unit area or unit volume and a preset mapping model, wherein the preset mapping model includes a mapping relationship between mass per unit area or unit volume and the dose distribution of the article under irradiation of a preset amount of energy; matching the dose distribution data with a fluoroscopy image of the article; and generating a radiation image of the article for displaying the dose distribution data matched with the fluoroscopy image of the article.

According to the foregoing embodiment of the aspect of the present disclosure, the radiation image is a planar image and the method further includes obtaining, when the article is scanned by X-rays, mass thickness data of the article under irradiation energy corresponding to the X-rays; classifying mass thickness values in the mass thickness data according to a mass thickness classification condition corresponding to the article, wherein the mass thickness classification condition is determined based on mapping relationship data between the mass thickness values and electron beam irradiation dose distribution data corresponding to the article; and generating, based on each mass thickness value, a classification of the mass thickness value and the electron beam irradiation dose distribution data, the radiation image for displaying the mass thickness values and the electron beam irradiation dose distribution data of the article.

According to any of the foregoing embodiments of the aspect of the present disclosure, the determination of the mass thickness classification condition includes determining a dose unevenness value corresponding to each mass thickness value based on the mapping relationship data; creating a mapping relationship curve based on each mass thickness value and the dose unevenness value corresponding to the mass thickness value; and determining multiple critical points in the mapping relationship curve, and classifying the mass thickness values into multiple classes based on the multiple critical points.

According to any of the foregoing embodiments of the aspect of the present disclosure, the determining multiple critical points in the mapping relationship curve includes determining, when the article is subjected to single-sided irradiation, the multiple critical points in the mapping relationship curve based on a preset maximum unevenness; and determining, when the article is subjected to double-sided irradiation, the multiple critical points in the mapping relationship curve based on the preset maximum unevenness and a valley value of the mapping relationship curve.

According to any of the foregoing embodiments of the aspect of the present disclosure, the generating, based on each mass thickness value, a classification of the mass thickness value and the electron beam irradiation dose distribution data, the radiation image for displaying the mass thickness values and the electron beam irradiation dose distribution data of the article includes assigning a display pattern corresponding to each mass thickness value based on each mass thickness value and the classification of the mass thickness value; and generating the radiation image of the article, based on the display pattern corresponding to each mass thickness value.

According to any of the foregoing embodiments of the aspect of the present disclosure, the generating, based on each mass thickness value, a classification of the mass thickness value and the electron beam irradiation dose distribution data, the radiation image for displaying the mass thickness values and the electron beam irradiation dose distribution data of the article further includes obtaining a mass thickness value corresponding to a target pixel point or a target area in the radiation image; querying, from the mapping relationship data, the electron beam irradiation dose distribution data corresponding to the mass thickness value of the target pixel point or the target area; and displaying the electron beam irradiation dose distribution data in the target area.

According to any of the foregoing embodiments of the aspect of the present disclosure, the generating, based on each mass thickness value, a classification of the mass thickness value and the electron beam irradiation dose distribution data, the radiation image for displaying the mass thickness values and the electron beam irradiation dose distribution data of the article further includes determining a dose unevenness value corresponding to the target pixel point or the target area, based on the electron beam irradiation dose distribution data corresponding to the mass thickness value of the target pixel point or the target area; determining irradiation effect based on a comparison result between the dose unevenness value and a preset maximum unevenness; and displaying the dose unevenness value and the irradiation effect in the target area.

According to any of the foregoing embodiments of the aspect of the present disclosure, the radiation image is a stereoscopic image and the method further includes constructing a standard dose distribution model, wherein the standard dose distribution model includes a standard mapping relationship between the dose distribution data and density values of the article under the irradiation of the preset amount of energy; performing the fluoroscopy scanning on the article, to obtain a stereoscopic fluoroscopy image of the article and a detected density value of each spatial point of the article; obtaining dose distribution data of each spatial point of the article, based on the detected density value of each spatial point of the article and the standard mapping relationship in the standard dose distribution model; and matching and displaying the dose distribution data of each spatial point of the article with the stereoscopic fluoroscopy image.

According to any of the foregoing embodiments of the aspect of the present disclosure, the constructing a standard dose distribution model includes constructing an initial dose distribution model, wherein the initial dose distribution model includes a theoretical mapping relationship between the dose distribution data and theoretical density values of the article under the irradiation of the preset amount of energy; obtaining a correction model; and obtaining the standard dose distribution model by correcting the initial dose distribution model with the correction model.

According to any of the foregoing embodiments of the aspect of the present disclosure, the obtaining a correction model includes providing a correction component matching the article, wherein the correction component includes multiple correction blocks of various sizes; performing a fluoroscopy scanning on the correction component to obtain theoretical density values of the correction component; measuring masses and sizes of the multiple correction blocks to calculate multiple real density values corresponding to the multiple correction blocks; and fitting the multiple real density values with the theoretical density values to obtain the correction model.

According to any of the foregoing embodiments of the aspect of the present disclosure, the fitting the multiple actual density values with the theoretical density values to obtain the correction model includes performing a polynomial fitting between the multiple real density values and the theoretical density values.

According to any of the foregoing embodiments of the aspect of the present disclosure, the multiple correction blocks are multiple cube correction blocks having a side length of 0.1 mm to 30 mm, and the multiple cube correction blocks of various sizes are to be spliced to form the correction component of a cuboid shape.

According to any of the foregoing embodiments of the aspect of the present disclosure, the dose distribution data includes at least one of the following items: ratio data of a maximum dose to a surface dose; ratio data of a minimum dose to the surface dose; and dose unevenness data.

According to any of the foregoing embodiments of the aspect of the present disclosure, the preset amount of energy is in a range of 1 MeV to 20 MeV.

In another aspect, an embodiment of the present disclosure provides an apparatus for detecting a dose distribution of an article. The apparatus includes a fluoroscopy unit configured to perform a fluoroscopy scanning on the article, to obtain mass data per unit area or unit volume for each point of the article; a data processing unit configured to obtain corresponding dose distribution data based on the mass data per unit area or unit volume and a preset mapping model, wherein the preset mapping model includes a mapping relationship between mass per unit area or unit volume and the dose distribution of the article under irradiation of a preset amount of energy; and an image processing unit configured to match the dose distribution data with a fluoroscopy image of the article, and generate a radiation image of the article for displaying the dose distribution data matched with the fluoroscopy image of the article.

According to any of the foregoing embodiments of the another aspect of the present disclosure, the fluoroscopy unit includes a data obtaining unit configured to obtain, when the article is scanned by X-rays, mass thickness data of the article under irradiation energy corresponding to the X-rays; the data processing unit includes a data classification unit configured to classify mass thickness values in the mass thickness data according to a mass thickness classification condition corresponding to the article, wherein the mass thickness classification condition is determined based on mapping relationship data between the mass thickness values and electron beam irradiation dose distribution data corresponding to the article; and the image processing unit includes an image generation unit configured to generate, based on each mass thickness value, a classification of the mass thickness value and the electron beam irradiation dose distribution data, the radiation image for displaying the mass thickness values and the electron beam irradiation dose distribution data of the article.

According to any of the foregoing embodiments of the another aspect of the present disclosure, the apparatus further includes a model processing device configured to construct a standard dose distribution model, wherein the standard dose distribution model includes a standard mapping relationship between the dose distribution data and density values of the article under the irradiation of the preset amount of energy; the fluoroscopy unit includes a stereoscopic fluoroscopy device configured to perform the fluoroscopy scanning on the article, to obtain the stereoscopic fluoroscopy image of the article and the detected density value of each spatial point of the article; the data processing unit includes a calculation device connected to the model processing device and the stereoscopic fluoroscopy device and configured to obtain the dose distribution data of each spatial point of the article, based on the detected density value of each spatial point of the article and the standard mapping relationship in the standard dose distribution model; and the image processing unit includes a display device connected to the calculation device and configured to match the dose distribution data of each spatial point of the article with the stereoscopic fluoroscopy image and display the dose distribution data of each spatial point of the article.

According to any of the foregoing embodiments of the another aspect of the present disclosure, the apparatus further includes a correction component configured to be subjected to a fluoroscopy scanning by the stereoscopic fluoroscopy unit to obtain a correction model, wherein the model processing unit is to construct an initial dose distribution model and obtain the standard dose distribution model by correcting the initial dose distribution model with the correction model.

According to any of the foregoing embodiments of the another aspect of the present disclosure, the correction component includes multiple correction blocks of various sizes, the multiple correction blocks are multiple cube correction blocks having a side length of 0.1 mm to 30 mm, and the multiple cube correction blocks of various sizes are to be spliced to form the correction component of a cuboid shape.

BRIEF DESCRIPTION OF THE DRAWINGS

To more clearly illustrate technical solutions of embodiments of the present disclosure, the accompanying drawings, which are to be referred by the embodiments of the present disclosure, will be briefly described. Those skilled in the art will be able to obtain additional drawings in accordance with these drawings without any creative work.

DETAILED DESCRIPTION

Various aspects of features and exemplary embodiments of the present disclosure will be described in detail below. The present disclosure will be provided in further detail below in conjunction with accompanying drawings and embodiments in order to make objects, technical solutions and advantages of the present disclosure to be more clearly understood. It is to be appreciated that the specific embodiments described herein are to be construed to illustrate the present disclosure but not to limit the present disclosure. It will be apparent to those skilled in the art that the present disclosure may be practiced without some of these specific details. The following description of the embodiments is merely to provide a better understanding of the present disclosure by illustrating examples thereof.

It is to be noted that relational terms such as first, second and the like are used herein only to distinguish an entity or operation from another entity or operation without requiring or implying that there is any such actual relationship or order between these entities or operations. Moreover, the term "comprise", "include" or any other variant thereof is intended to encompass a non-exclusive inclusion, such that a process, method, article or device that includes a series of elements includes not only these elements but also other elements that are not explicitly listed or those elements that are inherent to such a process, method, article or device. In the absence of more restrictions, elements defined by the statement "includes . . . " do not preclude the presence of additional identical elements in the process, method, article or device that includes the elements.

The embodiments of the present disclosure provide a method for detecting a dose distribution of an article, which may be a good guidance for the formulation of irradiation processing techniques.

Figure 1:
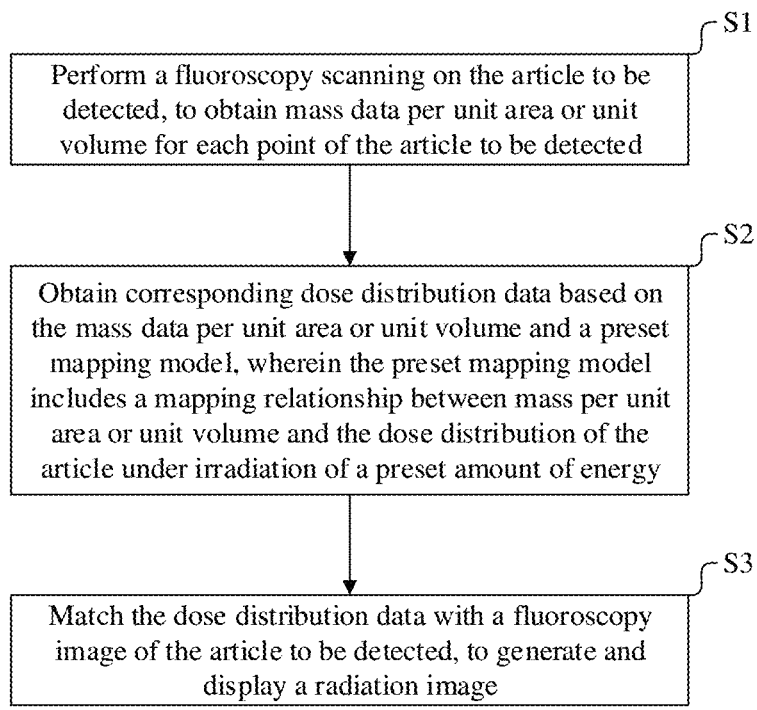
FIG. 1 is a flowchart of a method for detecting a dose distribution of an article according to an embodiment of the present disclosure.

FIG. 1 is a flowchart of a method for detecting a dose distribution of an article according to an embodiment of the present disclosure. The method for detecting the dose distribution of the article includes steps S1 to S3.

In step S1, a fluoroscopy scanning may be performed on an article to be detected, to obtain mass data per unit area or unit volume for each point of the article to be detected.

In step S2, corresponding dose distribution data may be obtained based on the mass data per unit area or unit volume and a preset mapping model. The preset mapping model may include a mapping relationship between the mass per unit area or unit volume and the dose distribution of the article under irradiation of a preset amount of energy.

In step S3, the dose distribution data may be matched with a fluoroscopy image of the article to be detected, so as to generate and display a radiation image.

According to the method for detecting the dose distribution of the article in the embodiment of the present disclosure, the dose distribution data of each point of the article to be detected may be matched with the fluoroscopy image to obtain and display the radiation image. In this way, the dose distribution data of each point of the article to be detected may be more intuitive and accurate, which may facilitate a reasonable configuration of various parameters in the irradiation processing. With the method for detecting the dose distribution of the article, the dose distribution inside the article may be clear at a glance, and operational efficiency at an irradiation processing site may be improved.

In the embodiment of the present disclosure, the mass data per unit area or unit volume may be the mass per unit area, that is, the mass thickness, or the mass per unit volume, that is, the (bulk) density. For ease of distinction, hereinafter, the "mass thickness" will represent the mass data per unit area and the "density" will represent the mass data per unit volume.

In the embodiment of the present disclosure, the fluoroscopy image of the article to be detected may be a planar image or a stereoscopic image. When the obtained mass data per unit area or unit volume of each point of the article to be detected is the mass thickness, the dose distribution data may be matched with a planar fluoroscopy image to obtain a planar (two-dimensional) radiation image. When the obtained mass data per unit area or unit volume of each point of the article to be detected is the density, the dose distribution data may be matched with a stereoscopic fluoroscopy image to obtain a stereoscopic (three-dimensional) radiation image.

The situation when the radiation image is a planar image will be described below. In some embodiments, the radiation image is a planar image, and the method for detecting the dose distribution of the article may be a radiation imaging method based on detection of a dose field.

Figure 2:
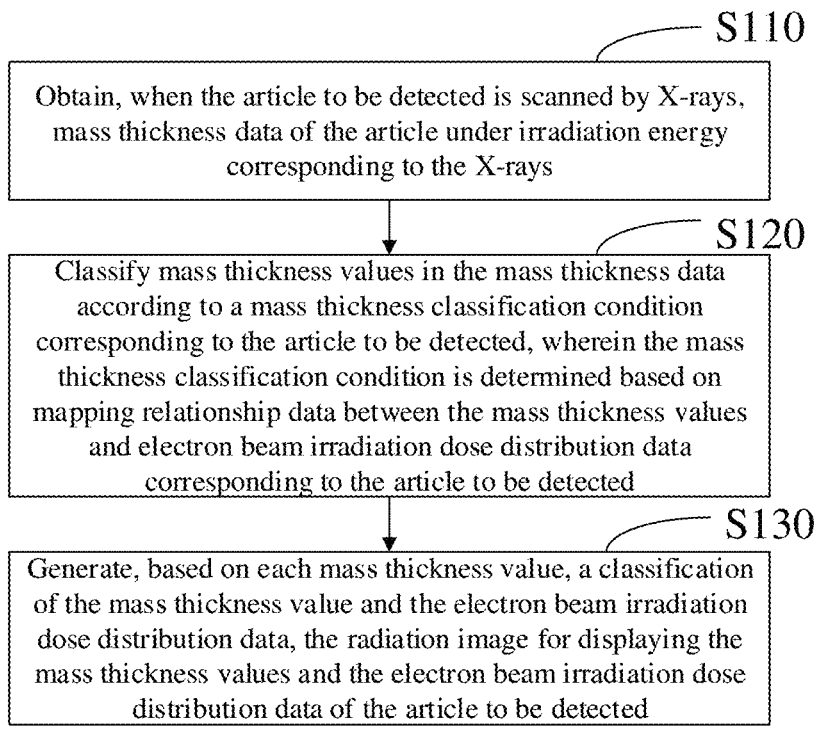
FIG. 2 is a schematic flowchart of a radiation imaging method according to an embodiment of the present disclosure.

FIG. 2 shows a schematic flowchart of a radiation imaging method according to an embodiment of the present disclosure. As shown in FIG. 2, the radiation imaging method may include steps S110 to S130.

S110: When the article to be detected is scanned by X-rays, the mass thickness data of the article to be detected may be obtained under irradiation energy corresponding to the X-rays.

S120: Mass thickness values in the mass thickness data may be classified according to a mass thickness classification condition corresponding to the article to be detected. The mass thickness classification condition may be determined based on mapping relationship data between the mass thickness values and electron beam irradiation dose distribution data corresponding to the article to be detected.

S130: According to each mass thickness value, its classification and the electron beam irradiation dose distribution data, a radiation image for displaying the mass thickness and the electron beam irradiation dose distribution data of the article to be detected may be generated.

Therefore, in the embodiment of the present disclosure, the mass thickness data of the article to be detected can be obtained, the mass thickness data of the article to be detected can be classified by directly using the mass thickness classification condition related to the electron beam irradiation dose distribution data, and then the radiation image can be generated according to each mass thickness value, its classification and the electron beam irradiation dose distribution data, so as to enable a tester to intuitively determine whether dose unevenness meets requirements according to the radiation image, improve test efficiency, and reduce test cost. In the embodiment of the present disclosure, the radiation image may include, for example, a mass thickness distribution map of the article to be detected.

In step S110 of the embodiment of the present disclosure, an X-ray device may be used as a scanning device. The X-ray device may emit X-rays having the same irradiation energy as the electron beam for the irradiation processing to scan the article to be detected, obtain radiation imaging conversion data, and calculate the mass thickness data of the article to be detected according to a conversion algorithm of the radiation imaging conversion data and the mass thickness data. The mass thickness data may include the mass thickness values corresponding to various positions of an X-ray irradiation surface of the article to be detected.

Figure 3:
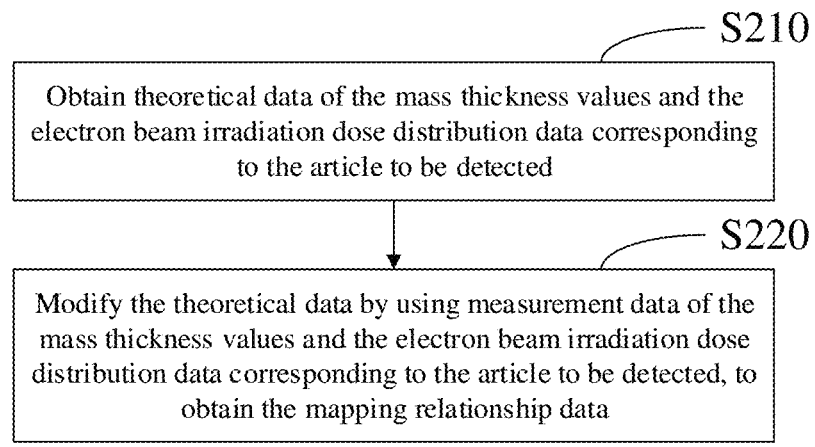
FIG. 3 is a schematic flowchart of a method for obtaining mapping relationship data according to an embodiment of the present disclosure.

FIG. 3 is a schematic flowchart of a method for obtaining mapping relationship data according to an embodiment of the present disclosure. As shown in FIG. 3, the method for obtaining the mapping relationship data may include steps S210 and S220.

S210: Theoretical data of the mass thickness values and the electron beam irradiation dose distribution data corresponding to the article to be detected may be obtained.

S220: The theoretical data may be modified by using measurement data of the mass thickness values and the electron beam irradiation dose distribution data corresponding to the article to be detected, to obtain the mapping relationship data.

In step S210 of the embodiment of the present disclosure, the Monte Carlo algorithm may be used to obtain the theoretical data of the mass thickness values and the electron beam irradiation dose distribution data corresponding to the article to be detected, when simulated material corresponding to the article to be detected is irradiated by an electron beam having the same irradiation energy as the electron beam for the irradiation processing. The irradiation energy of the electron beam for the irradiation processing may be in a range of 1~20 MeV.

In the embodiment of the present disclosure, the electron beam irradiation dose distribution data may include data such as a ratio of a maximum dose to a surface dose, a ratio of a minimum dose to the surface dose, and the dose unevenness.

In step S220 of the embodiment of the present disclosure, when a real product corresponding to the article to be detected is irradiated by an electron beam having the same irradiation energy as the electron beam for the irradiation processing, the measurement data of the mass thickness values and the electron beam irradiation dose distribution data corresponding to the article to be detected may be obtained. Then, the theoretical data and the measurement data may be fitted using Excel or MATLAB data processing software to obtain a fitting formula, and the fitting formula may be used to modify the theoretical data. The modified data is the mapping relationship data. Specifically, the fitting formula may be a polynomial fitting, such as a linear fitting, an exponential fitting, a power fitting, and a logarithmic fitting.

Figure 4:
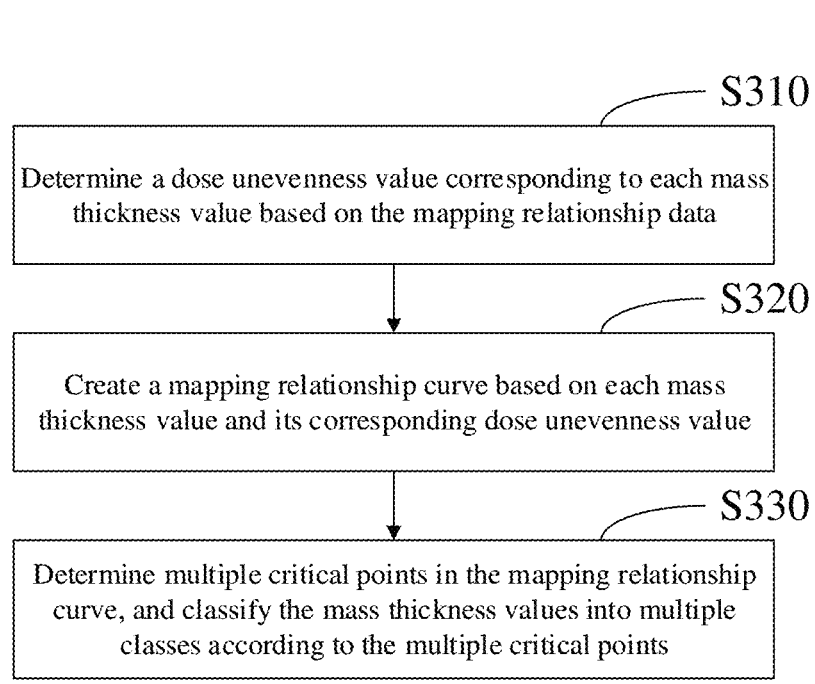
FIG. 4 is a schematic flowchart of a method for determining a mass thickness classification condition according to an embodiment of the present disclosure.

FIG. 4 is a schematic flowchart of a method for determining a mass thickness classification condition provided by an embodiment of the present disclosure. As shown in FIG. 4, the method for determining the mass thickness classification condition may include steps S310 to S330.

S310: A dose unevenness value corresponding to each mass thickness value may be determined based on the mapping relationship data.

S320: A mapping relationship curve may be created based on each mass thickness value and its corresponding dose unevenness value.

S330: Multiple critical points in the mapping relationship curve may be determined, and the mass thickness values may be classified into multiple classes according to the multiple critical points.

In step S310 of the embodiment of the present disclosure, the ratio of the maximum dose to the surface dose in the electron beam irradiation dose distribution data corresponding to the mass thickness values may be divided by the ratio of the minimum dose to the surface dose, to obtain the dose unevenness value corresponding to each mass thickness value.

Figure 5:
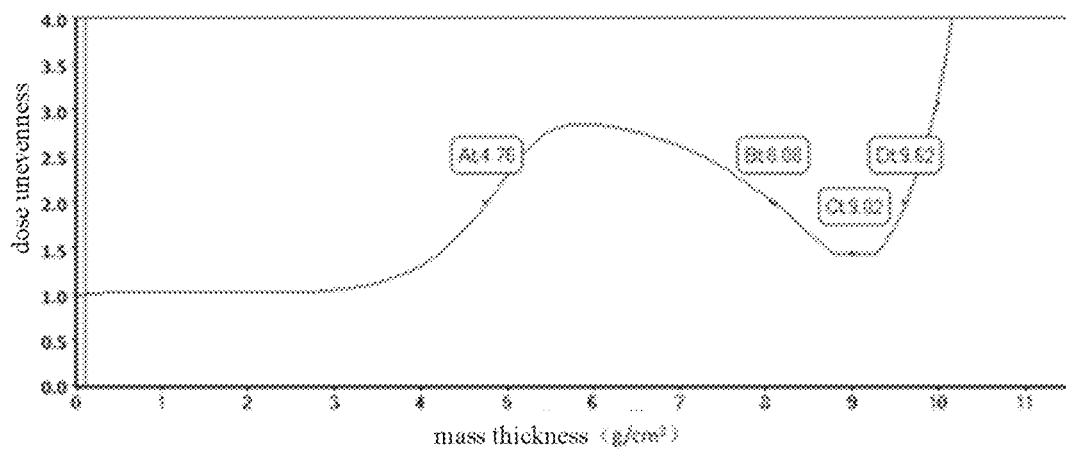
FIG. 5 is a graph of the mapping relationship for double-sided irradiation in an embodiment of the present disclosure.
Figure 6:
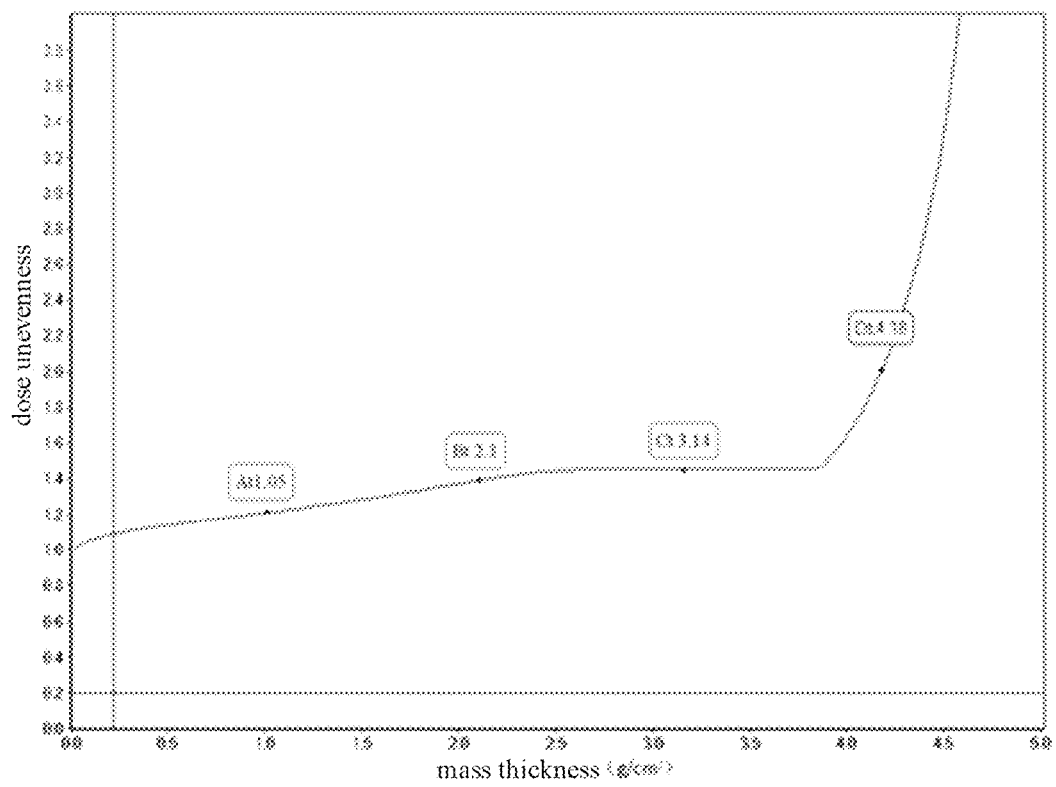
FIG. 6 is a graph of the mapping relationship for single-sided irradiation in an embodiment of the present disclosure.

In step S320 of the embodiment of the present disclosure, the mass thickness values may be represented as abscissas and the dose unevenness values may be represented as ordinates, and the mapping relationship curve (mass thickness—dose unevenness curve) may be created by fitting the mass thickness values with corresponding dose unevenness values. FIG. 5 shows the mapping relationship curve for double-sided irradiation. FIG. 6 shows the mapping relationship curve for single-sided irradiation.

In step S330 of the embodiment of the present disclosure, the multiple critical points in the mapping relationship curve may be determined as follows.

When the article is subjected to single-sided irradiation, the multiple critical points in the mapping relationship curve may be determined according to a preset maximum unevenness;

When the article is subjected to double-sided irradiation, the multiple critical points in the mapping relationship curve may be determined according to the preset maximum unevenness and a valley value of the mapping relationship curve.

Specific methods for determining the critical points will be described in detail by referring to the two cases of double-sided irradiation and single-sided irradiation.

The First Case (Double-Sided Irradiation)

In this case, the mass thickness values corresponding to the preset maximum unevenness may be respectively determined as the critical points At, Bt, Dt, and then the valley value between the critical point Bt and the critical point Dt may be determined as the critical point Ct.

The specific position of the critical point Ct may be determined as follows: the mapping relationship curve monotonously rises to the highest point, then starts to monotonously fall, and arrives at the lowest point; there is a small region on both sides of the lowest point where the value does not change much; and the mass thickness corresponding to the end of the region may be selected as the critical point Ct. After the critical point Ct, the mapping relationship curve again shows a fast monotonous rising pattern. Therefore, the specific method for determining the critical point Ct may include: finding the minimum value of the monotonically decreasing dose unevenness values in the mapping relationship curve; the dose unevenness values of adjacent points after the minimum value may be subtracted from each other; when a difference having an absolute value greater than or equal to 0.01 is obtained, the mass thickness value corresponding to the dose unevenness value may be determined as the critical point Ct.

The Second Case (Single-Sided Irradiation)

In this case, the mass thickness value corresponding to the preset maximum unevenness may be determined as the critical point Dt, and then the mass thickness values before the critical point Dt may be equally divided to get three equidistant points. The three equidistant points may be the critical points At, Bt, and Ct.

In step S330 of the embodiment of the present disclosure, the mass thickness values can be divided into five classes of mass thicknesses A, B, C, D, and E according to the critical points At, Bt, Ct, and Dt. Among them, the mass thicknesses of class A may include the mass thickness values between 0 and the critical point At, the mass thicknesses of class B may include the mass thickness values between the critical point At and the critical point Bt, the mass thicknesses of class C may include the mass thickness values between the critical point Bt and the critical point Ct, the mass thicknesses of class D may include the mass thickness values between the critical point Ct and the critical point Dt, and the mass thicknesses of class E may include the mass thickness values greater than the critical point Dt.

When the article to be detected is subjected to the single-sided irradiation, only the dose unevenness values corresponding to the mass thicknesses of class E do not meet the requirements, and the electron beam cannot penetrate the article to be detected. When the article to be detected is subjected to the double-sided irradiation, the mass thicknesses of class A can be used for the double-sided irradiation and the irradiation of a single surface dose can be reduced; the mass thicknesses of class B can be penetrated by the double-sided irradiation but the dose unevenness values may be relatively high; the mass thicknesses of class C may be a range of mass thicknesses that is better for the double-sided irradiation; the mass thicknesses of class D may be a range of mass thickness that is feasible for the double-sided irradiation; the mass thickness of class E correspond to the dose unevenness values that do not meet the requirements, and the electron beam cannot penetrate the article to be detected.

Figure 7:
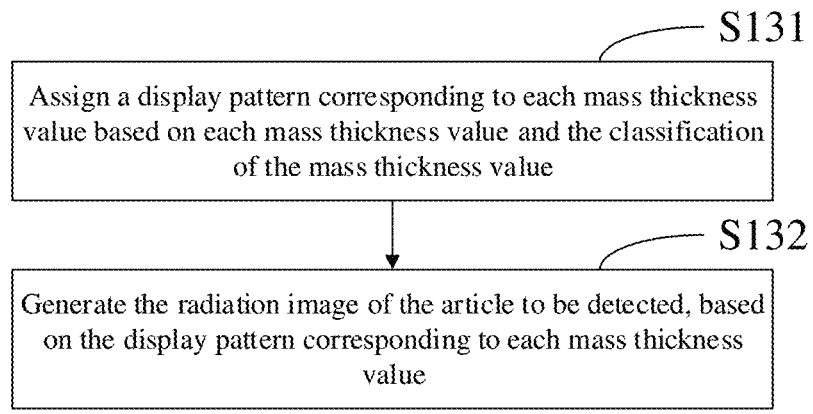
FIG. 7 is a schematic flowchart of a method for generating a radiation image of an article to be detected according to an embodiment of the present disclosure.

FIG. 7 is a schematic flowchart of a method for generating a radiation image of an article to be detected according to an embodiment of the present disclosure. As shown in FIG. 7, step S130 of generating the radiation image for displaying the mass thickness and the electron beam irradiation dose distribution data of the article to be detected according to each mass thickness value, its classification and the electron beam irradiation dose distribution data may include steps S131 and S132.

S131: A display pattern corresponding to each mass thickness value may be assigned based on each mass thickness value and its classification.

S132: The radiation image of the article to be detected may be generated based on the display pattern corresponding to each mass thickness value.

In step S131 of the embodiment of the present disclosure, a color and a color depth corresponding to each mass thickness value may be assigned based on each mass thickness value and its classification. For example, the color for the mass thicknesses of class A may be green, the color for the mass thicknesses of class B may be blue, the color for the mass thicknesses of class C may be yellow, the color for the mass thicknesses of class D may be red, and the color for the mass thicknesses of class E may be black. Meanwhile, in each class of mass thicknesses, the greater the mass thickness value is, the deeper the color depth corresponding to the mass thickness value is, and the smaller the mass thickness value is, the lighter the color depth corresponding to the mass thickness value is.

In step S132 of the embodiment of the present disclosure, the radiation image of the article to be detected may be generated based on the color and the color depth determined in step S131.

Figure 8:
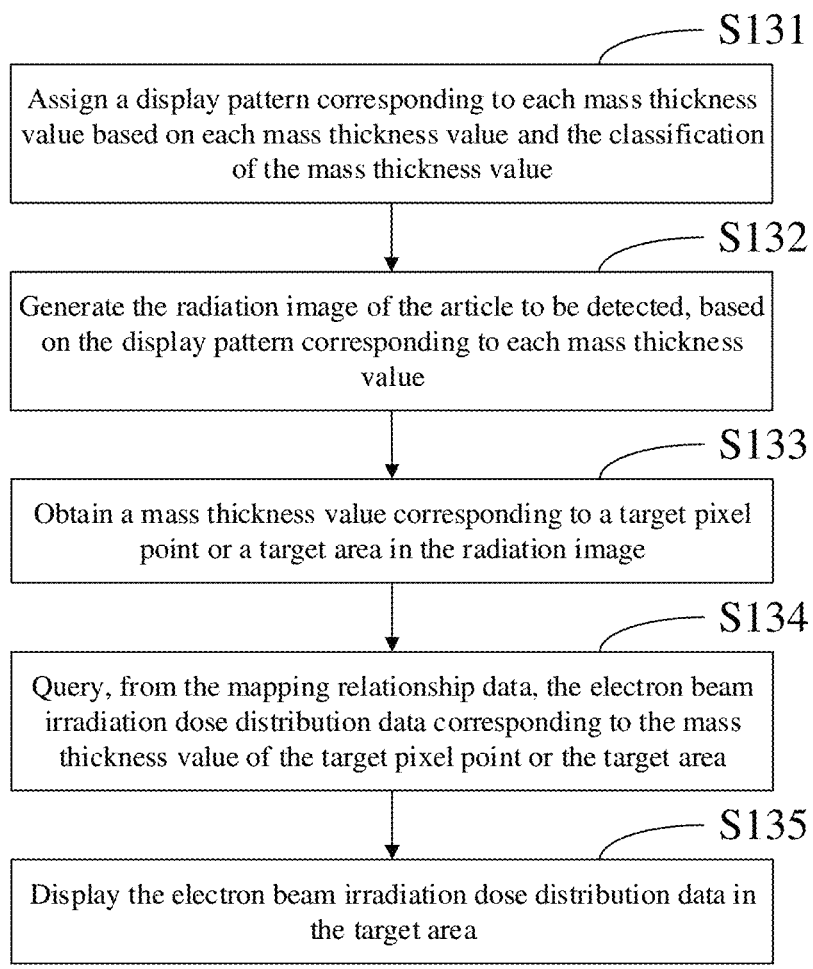
FIG. 8 is a schematic flowchart of a method for generating a radiation image of an article to be detected according to another embodiment of the present disclosure.

FIG. 8 is a schematic flowchart of a method for generating a radiation image of an article to be detected according to another embodiment of the present disclosure. As shown in FIG. 8, step S130 of generating the radiation image for displaying the mass thickness and the electron beam irradiation dose distribution data of the article to be detected according to each mass thickness value, its classification and the electron beam irradiation dose distribution data may further include steps S133 to S135.

S133: The mass thickness value corresponding to a target pixel point or a target area in the radiation image may be obtained.

S134: The electron beam irradiation dose distribution data corresponding to the mass thickness value may be queried from the mapping relationship data.

S135: The electron beam irradiation dose distribution data may be displayed in the target area.

In the embodiment of the present disclosure, the tester can select the target pixel point or the target area in the radiation image that the tester may want to view detailed data. After determining the mass thickness value of the target pixel point or the target area, the electron beam irradiation dose distribution data corresponding to the mass thickness value, such as the ratio of the maximum dose to the surface dose, the ratio of the minimum dose to the surface dose, the dose unevenness, and the like, may be displayed in the target area.

Figure 9:
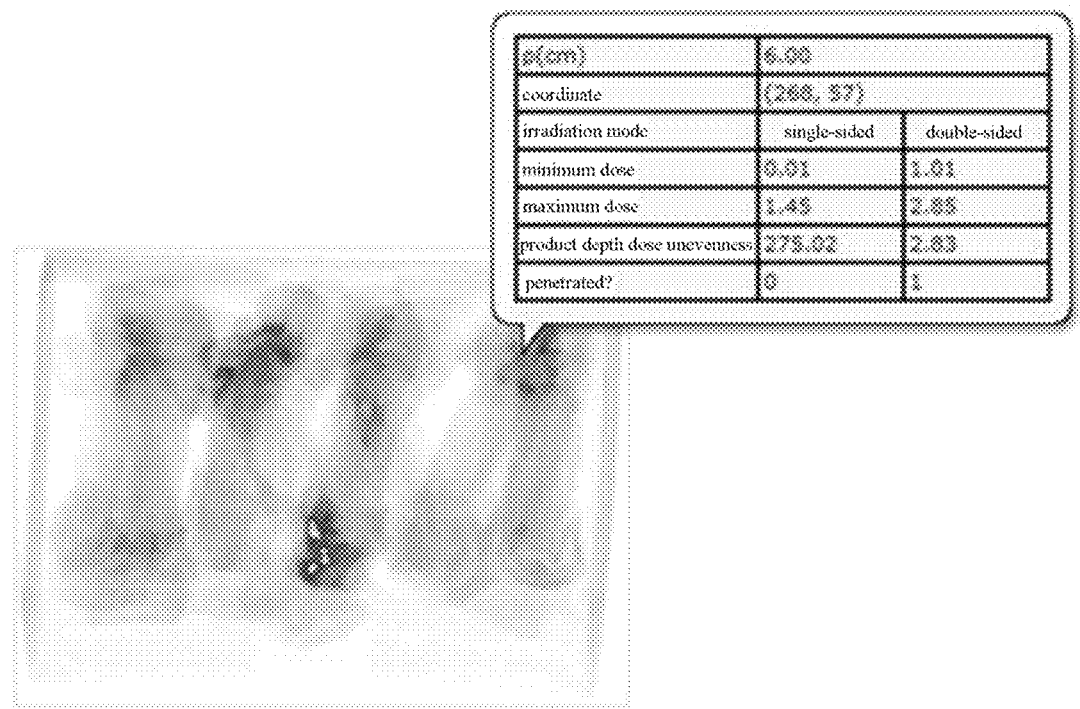
FIG. 9 is a positional relationship diagram of a radiation image and a target area according to an embodiment of the present disclosure.

In the embodiment of the present disclosure, the relative position of the target area and the radiation image may be shown in FIG. 9, and the electron beam irradiation dose distribution data is displayed in a table format. In another embodiment, the target area may also be set at an edge of the radiation image without blocking the radiation image. In other embodiments of the present disclosure, the target area may also be set inside the radiation image.

Figure 10:
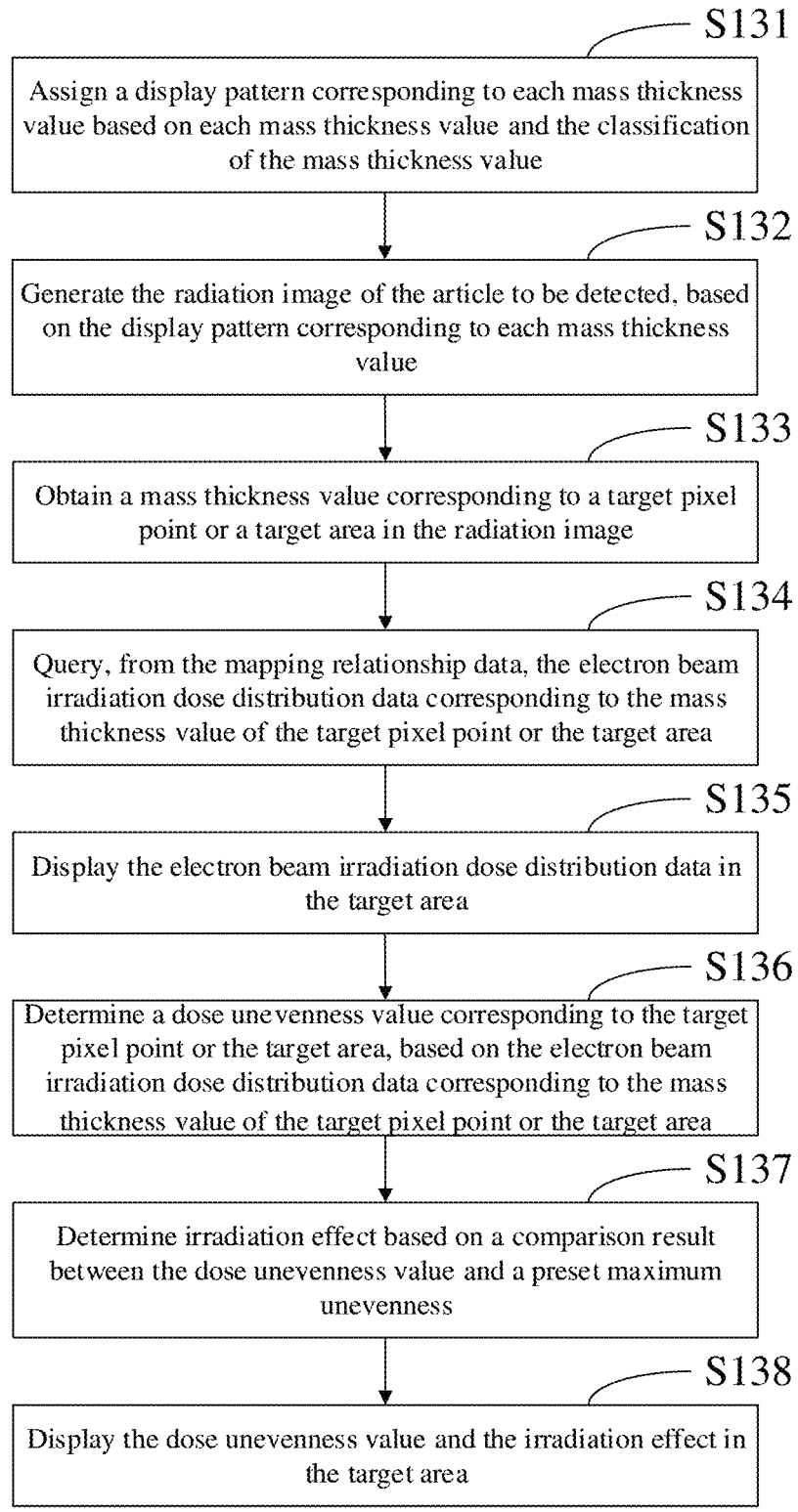
FIG. 10 is a schematic flowchart of a method for generating a radiation image of an article to be detected according to a further embodiment of the present disclosure.

FIG. 10 is a schematic flowchart of a method for generating a radiation image of an article to be detected according to a further embodiment of the present disclosure. As shown in FIG. 10, step S130 of generating the radiation image for displaying the mass thickness and the electron beam irradiation dose distribution data of the article to be detected according to each mass thickness value, its classification and the electron beam irradiation dose distribution data may further include steps S136 to S138.

S136: The dose unevenness value corresponding to the target pixel point or the target area may be determined based on the electron beam irradiation dose distribution data corresponding to the mass thickness value.

S137: Irradiation effect may be determined based on a comparison result between the dose unevenness value and the preset maximum unevenness.

S138: The dose unevenness value and the irradiation effect may be displayed in the target area.

In the embodiment of the present disclosure, a specific process of performing radiation imaging on a cargo using the radiation imaging method may include five steps as follows.

First step: Prepare the cargo which can be boxes or bulk articles.

Second step: Put the cargo in an X-ray device for scanning.

Third step: Generate the radiation image by the radiation imaging method.

Fourth step: Display the radiation image.

Fifth step: Display the electron beam irradiation dose distribution data of the target pixel point.

The situation when the radiation image is a stereoscopic image will be described below. In some embodiments, the radiation image is a stereoscopic image, and the method for detecting the dose distribution of the article may be a method for detecting a spatial dose distribution of an article.

Figure 11:
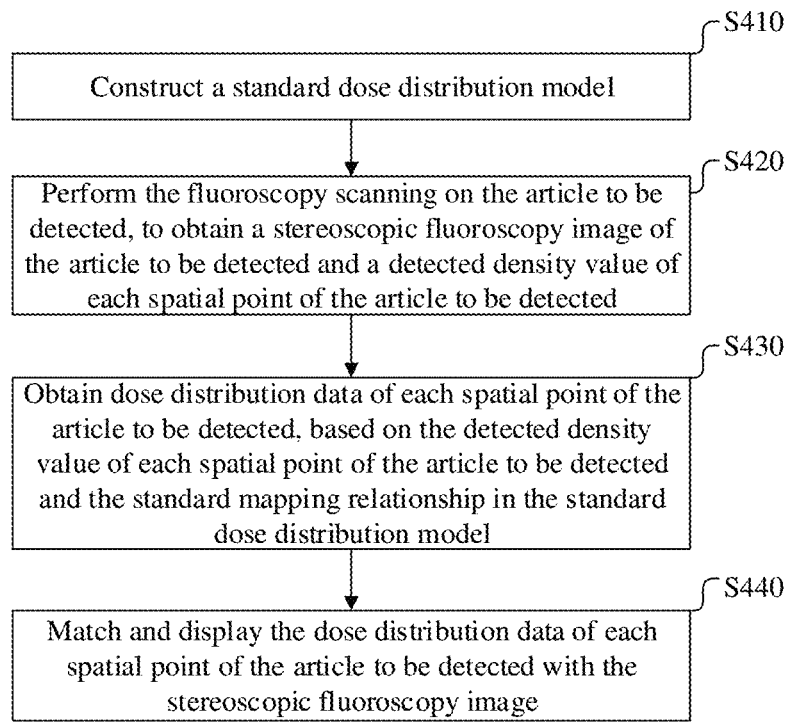
FIG. 11 shows a flowchart of a method for detecting a spatial dose distribution of an article according to an embodiment of the present disclosure.

FIG. 11 shows a flowchart of a method for detecting a spatial dose distribution of an article according to an embodiment of the present disclosure. The method for detecting the spatial dose distribution of the article may include steps S410 to S440.

In step S410, a standard dose distribution model may be constructed. The standard dose distribution model may include a standard mapping relationship between dose distribution data and density values of the article under irradiation of a preset amount of energy.

The preset amount of energy may be an energy of 1 MeV to 20 MeV. The dose distribution data may include at least any one of: ratio data of the maximum dose to the surface dose; ratio data of the minimum dose to the surface dose; dose unevenness data. That is, the standard dose distribution model may include at least any one of: a standard mapping relationship between the ratio data of the maximum dose to the surface dose and the density values; a standard mapping relationship between the ratio data of the minimum dose to the surface dose and the density values; a standard mapping relationship between the dose unevenness data and the density values.

Figure 12:
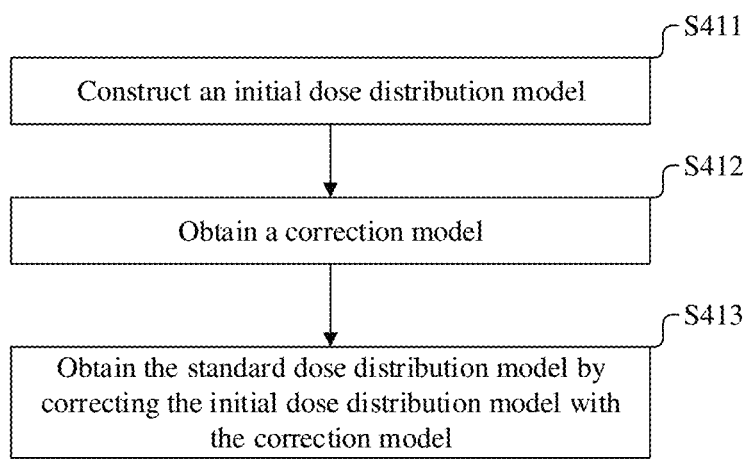
FIG. 12 is a flowchart of a step of constructing a standard dose distribution model in a method for detecting a spatial dose distribution of an article according to an embodiment of the present disclosure.

FIG. 12 is a flow chart of the step of constructing the standard dose distribution model in the method for detecting the spatial dose distribution of the article according to an embodiment of the present disclosure. In step S410 of this embodiment, the step of constructing the standard dose distribution model may include the following steps S411 to step S413.

In step S411, an initial dose distribution model may be constructed. The initial dose distribution model may include a theoretical mapping relationship between the dose distribution data and theoretical density values of the article under the irradiation of the preset amount of energy.

In some embodiments, a Monte Carlo or simulation software may be used to simulate a correspondence relationship between the theoretical density value and the dose distribution data for each energy range of electron beams versus each spatial point of the article, and establish a model of the dose distribution data and the theoretical density values for different positions (spatial points) of the article.

In step S412, a correction model is obtained. The correction model may be a correction factor or a correction formula.

Figure 13:
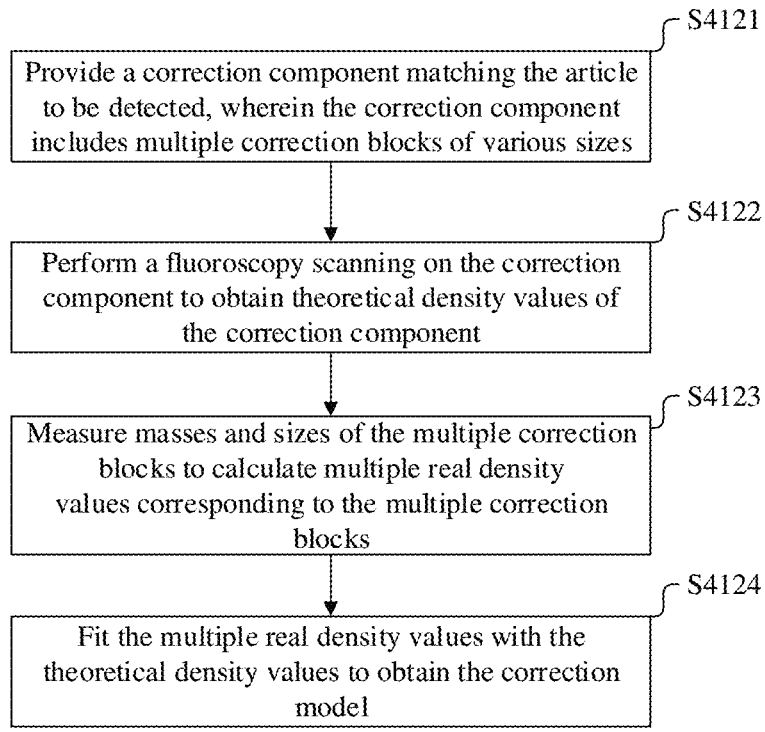
FIG. 13 is a flowchart of a step of obtaining a correction model in a method for detecting a spatial dose distribution of an article according to an embodiment of the present disclosure.

FIG. 13 is a flowchart of the step of obtaining the correction model in the method for detecting the spatial dose distribution of the article according to an embodiment of the present disclosure. The step of obtaining the correction model may further include steps S4121 to S4124.

In step S4121, a correction component matching the article to be detected may be provided. The correction component may include multiple correction blocks of various sizes. The correction component may be made of common materials used in irradiation processing. For example, in this embodiment, homogeneous plexiglass may be selected to make the correction component.

In some embodiments, the correction block may be a cube correction block. A side length of the cube correction block may be 0.1 mm to 30 mm Multiple cube correction blocks of various sizes may be spliced to form a cuboid correction component.

In step S4122, a fluoroscopy scanning may be performed on the correction component to obtain the theoretical density values of the correction component. In some embodiments, a dual-energy X-ray tube scanning correction component may be used and its image and theoretical density values may be obtained simultaneously.

In step S4123, masses and sizes of the multiple correction blocks may be measured, and multiple real density values corresponding to the multiple correction blocks may be calculated.

In step S4124, the multiple real density values may be fitted with the theoretical density values to obtain the correction model.

Here, fitting the multiple real density values with the theoretical density values may include a polynomial fitting between the multiple real density values and the theoretical density values, such as a linear fitting, an exponential fitting, a power fitting, a logarithmic fitting, etc. The obtained fitting formula may be the correction model in form of a correction formula, and the obtained value may be the correction model in form of a correction factor.

The following example illustrates a process for obtaining the correction model. As described above, the correction component may be formed by splicing a plurality of cube correction blocks of various sizes. The correction component formed by splicing may be a cuboid with uniform length and width. A plurality of spatial points corresponding to the plurality of correction blocks may be obtained from inside of the correction component. For example, 22 points may be obtained. The theoretical density value of the multiple spatial points may be obtained by X-ray technology fluoroscopy scanning. Through practical measurement, multiple real density values corresponding to multiple correction blocks, (i.e., corresponding to multiple spatial points) may be obtained.

Generally, the multiple real density values may be multiple scatter points that coincide with the theoretical density values or are distributed near the theoretical density values. In some embodiments, multiple differential values between the multiple real density values and the theoretical density values may be calculated, and then the multiple differential values may be fitted with the corresponding scatter points. Polynomial fitting may be used to obtain the fitted formula as the correction model in form of the correction formula.

It can be understood that the above process is only an example process of obtaining the correction model. In some other embodiments, the shape and number of the correction blocks in the correction component may be set as needed, and the fitting method is not limited to the above-mentioned polynomial fitting by calculating the differential values, but may also be other fittings by calculating quotients.

After the above steps, the correction model may be obtained. Then, in step S413, the initial dose distribution model may be corrected by the correction model to obtain the standard dose distribution model.

The correction model is a correction model associated with the density value. Therefore, in the process of correcting the initial dose distribution model to the standard dose distribution model, the theoretical mapping relationship between the dose distribution data and the theoretical density values may be corrected to obtain the standard mapping relationship that represents a more realistic correspondence between the dose distribution data and the density values.

As such, the standard dose distribution model may be obtained.

Continue to refer to FIG. 11. In step S420, a fluoroscopy scanning may be performed on the article to be detected, to obtain a stereoscopic fluoroscopy image of the article to be detected and a detected density value of each spatial point of the article to be detected.

In step S420, the article to be detected may be subjected to a comprehensive tomography scanning by receiving X-rays of a certain energy. In some embodiments, a dual-energy X-ray tube may be rotated around the article to be detected to scan the article and obtain a stereoscopic fluoroscopy image of the article to be detected. Detectors may be arranged in multiple columns along a vertical axis direction to form a two-dimensional detector array. The signals collected by the detectors may be processed into data by a computer to obtain the stereoscopic fluoroscopy image of the article to be detected and a detected density value of each spatial point of the article to be detected.

In step S430, the dose distribution data of each spatial point of the article to be detected may be obtained according to the detected density value of each spatial point of the article to be detected and the standard mapping relationship in the standard dose distribution model. Because the standard dose distribution model is obtained by correcting the constructed initial dose distribution model, the mapping relationship between the dose distribution data and the density values in the standard dose distribution model may be more accurate, which further makes the obtained dose distribution data of each spatial point more accurate.

In step S440, the dose distribution data of each spatial point of the article to be detected may be matched and displayed with the stereoscopic fluoroscopy image. In some embodiments, other data such as the density value of each spatial point of the article to be detected may also be matched and displayed with the stereoscopic fluoroscopy image.

In some embodiments, a suitable application interface may be developed to display an ultra-high-definition three-dimensional image. In the application interface, a fluoroscopy image of an interior of the article to be detected may be viewed from any angle, and fault cross-section information of the interior of the article to be detected may be displayed.

According to the method for detecting the spatial dose distribution of the article in the embodiment of the present disclosure, the result of the detected dose distribution information of the article to be detected can be graphically displayed and output as data. The dose distribution information may include the ratio of the maximum dose to the surface dose, the ratio of the minimum dose to the surface dose, and the dose unevenness of the article to be detected and each unit inside. In this way, analysis results and suggested schemes can be provided for the subsequent irradiation processing of the article to be detected. For example, suggestions about whether the article to be detected is suitable for irradiation, a dose distribution level, and the like can be provided.

According to the method for detecting the spatial dose distribution of the article in the embodiment of the present disclosure, the dose distribution data of each spatial point of the article to be detected may be matched with the stereoscopic fluoroscopy image to obtain a three-dimensional stereoscopic radiation image, and image information of each spatial point of the article to be detected and the dose distribution data may be displayed. In this way, the dose distribution data of each spatial point of the article to be detected may be more intuitive and accurate, which may facilitate a reasonable configuration of various parameters in the irradiation processing. Compared with conventional techniques, the method for detecting the spatial dose distribution of the article may have the advantages of short test cycle, high speed and efficiency, high accuracy of test results, and clear internal conditions of the article, which can greatly improve the operational efficiency at the irradiation processing site.

The embodiments of the present disclosure also provide an apparatus for detecting a dose distribution of an article. The apparatus may be used to detect the dose distribution of the article to be detected.

Figure 14:
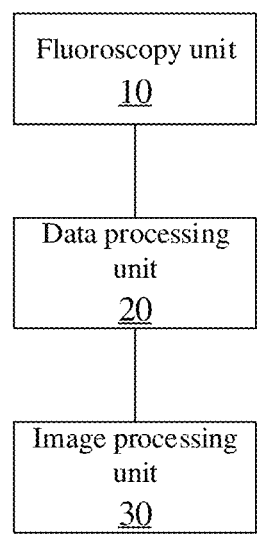
FIG. 14 is a structural block diagram of an apparatus for detecting a dose distribution of an article according to an embodiment of the present disclosure.

FIG. 14 is a structural block diagram of an apparatus for detecting a dose distribution of an article according to an embodiment of the present disclosure. The apparatus may include a fluoroscopy unit 10, a data processing unit 20, and an image processing unit 30.

The fluoroscopy unit 10 may be configured to perform a fluoroscopy scanning on the article to be detected, to obtain mass data per unit area or unit volume for each point of the article to be detected.

The data processing unit 20 may be configured to obtain corresponding dose distribution data based on the mass data per unit area or unit volume and a preset mapping model, wherein the preset mapping model includes a mapping relationship between mass per unit area or unit volume and the dose distribution of the article under irradiation of a preset amount of energy.

The image processing unit 30 may be configured to match the dose distribution data with a fluoroscopy image of the article to be detected, to generate and display a radiation image.

According to the apparatus for detecting the dose distribution of the article according to the embodiment of the present disclosure, the dose distribution data of each point of the article to be detected may be matched with the fluoroscopy image to obtain and display the radiation image. In this way, the dose distribution data of each point of the article to be detected may be more intuitive and accurate, which may facilitate a reasonable configuration of various parameters in the irradiation processing. By use of the apparatus to detect the dose distribution of the article, the dose distribution inside the article may be clear at a glance, and operational efficiency at an irradiation processing site may be improved.

The situation when the obtained radiation image is a planar image will be described below. In some embodiments, the radiation image is a planar image, and the apparatus for detecting the dose distribution of the article may be a radiation imaging device based on detection of a dose field.

Figure 15:
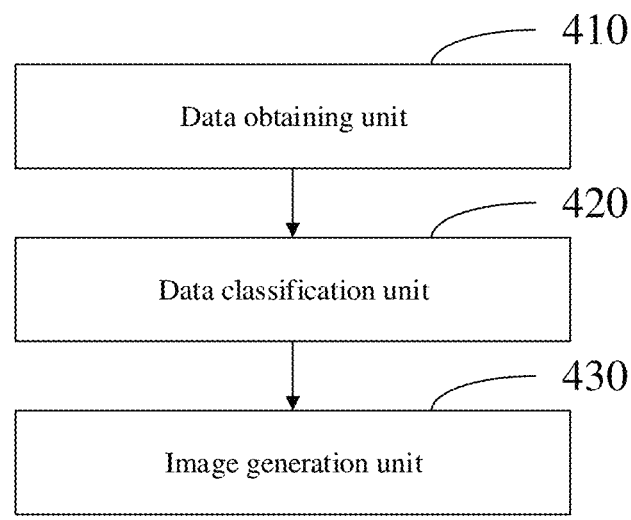
FIG. 15 is a schematic structural diagram of a radiation imaging device according to an embodiment of the present disclosure.

FIG. 15 is a schematic structural diagram of a radiation imaging device according to an embodiment of the present disclosure. As shown in FIG. 15, the radiation imaging device may include a data obtaining unit 410, a data classification unit 420 and an image generation unit 430.

The data obtaining unit 410 may be configured to obtain, when the article to be detected is scanned by X-rays, mass thickness data of the article under irradiation energy corresponding to the X-rays.

The data classification unit 420 may be configured to classify mass thickness values in the mass thickness data according to a mass thickness classification condition corresponding to the article to be detected, wherein the mass thickness classification condition is determined based on mapping relationship data between the mass thickness values and electron beam irradiation dose distribution data corresponding to the article to be detected.

The image generation unit 430 may be configured to generate, based on each mass thickness value, a classification of the mass thickness value and the electron beam irradiation dose distribution data, the radiation image for displaying the mass thickness values and the electron beam irradiation dose distribution data of the article to be detected.

That is, in the apparatus for detecting the dose distribution of the article, the fluoroscopy unit may include the data obtaining unit, the data processing unit may include the data classification unit, and the image processing unit may include the image generation unit.

Therefore, in the embodiment of the present disclosure, the mass thickness data of the article to be detected can be obtained, the mass thickness data of the article to be detected can be classified by directly using the mass thickness classification condition related to the electron beam irradiation dose distribution data, and then the radiation image can be generated according to each mass thickness value, its classification and the electron beam irradiation dose distribution data, so as to enable a tester to intuitively determine whether dose unevenness meets requirements according to the radiation image, improve test efficiency, and reduce test cost.

In the embodiment of the present disclosure, the radiation imaging device may further include a condition determination unit configured to determine the mass thickness classification condition based on the mapping relationship data between the mass thickness values and the electron beam irradiation dose distribution data corresponding to the article to be detected.

In the embodiment of the present disclosure, the condition determination unit may be further configured to obtain theoretical data of the mass thickness values and the electron beam irradiation dose distribution data corresponding to the article to be detected; and modify the theoretical data by using measurement data of the mass thickness values and the electron beam irradiation dose distribution data corresponding to the article to be detected, to obtain the mapping relationship data.

In the embodiment of the present disclosure, the condition determination unit may be further configured to determine a dose unevenness value corresponding to each mass thickness value based on the mapping relationship data; create a mapping relationship curve based on each mass thickness value and the dose unevenness value corresponding to the mass thickness value; determine multiple critical points in the mapping relationship curve and classify the mass thickness values into multiple classes based on the multiple critical points.

In the embodiment of the present disclosure, the image generation unit 430 may be further configured to assign a display pattern corresponding to each mass thickness value based on each mass thickness value and the classification of the mass thickness value; and generate the radiation image of the article to be detected based on the display pattern corresponding to each mass thickness value.

In the embodiment of the present disclosure, the image generation unit 430 may be further configured to obtain the mass thickness value corresponding to a target pixel point or a target area in the radiation image; query the electron beam irradiation dose distribution data corresponding to the mass thickness value from the mapping relationship data; and display the electron beam irradiation dose distribution data in the target area.

In an embodiment of the present disclosure, the image generation unit 430 may be further configured to determine a dose unevenness value corresponding to the target pixel point or the target area based on the electron beam irradiation dose distribution data corresponding to the mass thickness value; determine irradiation effect based on a comparison result between the dose unevenness value and a preset maximum unevenness; and display the dose unevenness value and the irradiation effect in the target area.

The situation when the obtained radiation image is a stereoscopic image will be described below. In some embodiments, the radiation image is a stereoscopic image, and the apparatus for detecting the dose distribution of the article may be an apparatus for detecting a spatial dose distribution of an article.

Figure 16:
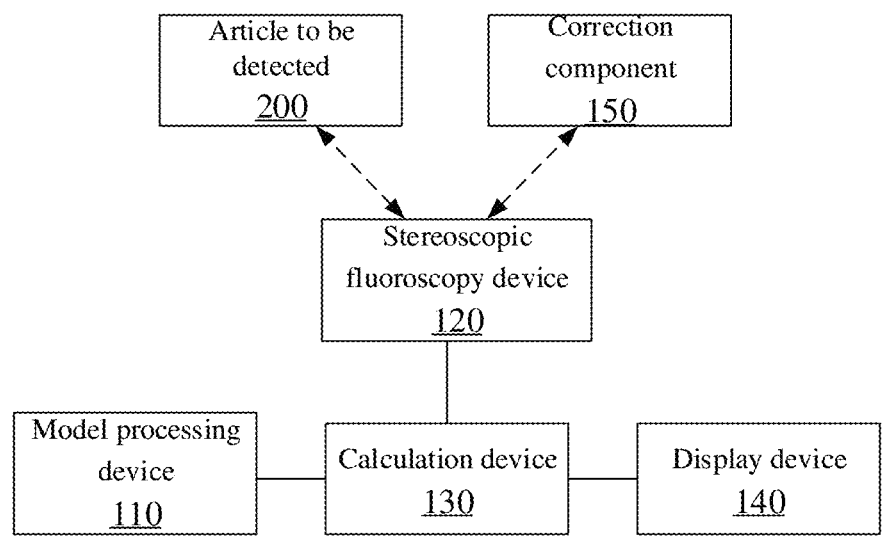
FIG. 16 is a structural block diagram of an apparatus for detecting a spatial dose distribution of an article according to an embodiment of the present disclosure.

FIG. 16 is a structural block diagram of an apparatus for detecting a spatial dose distribution of an article according to an embodiment of the present disclosure. The apparatus may include a model processing device 110, a stereoscopic fluoroscopy device 120, a calculation device 130, and a display device 140.

The model processing device 110 may be configured to construct a standard dose distribution model. The standard dose distribution model may include a standard mapping relationship between the dose distribution data and density values of the article under the irradiation of the preset amount of energy.

The stereoscopic fluoroscopy device 120 may be configured to perform the fluoroscopy scanning on the article 200 to be detected, to obtain the stereoscopic fluoroscopy image of the article 200 to be detected and the detected density value of each spatial point of the article 200 to be detected.

The calculation device 130 may be connected to the model processing device 110 and the stereoscopic fluoroscopy device 120 and configured to obtain the dose distribution data of each spatial point of the article 200 to be detected, based on the detected density value of each spatial point of the article 200 to be detected and the standard mapping relationship in the standard dose distribution model.

The display device 140 may be connected to the calculation device 130 and configured to match the dose distribution data of each spatial point of the article 200 to be detected with the stereoscopic fluoroscopy image and display the dose distribution data of each spatial point of the article 200 to be detected.

That is, the apparatus for detecting the dose distribution of the article may further include the model processing device, the fluoroscopy unit may include the stereoscopic fluoroscopy device, the data processing unit may include the calculation device, and the image processing unit may include the display device.

In some embodiments, the apparatus for detecting the dose distribution of the article may further include a correction component 150 configured to be subjected to a fluoroscopy scanning by the stereoscopic fluoroscopy unit 120 to obtain a correction model. The model processing device 110 is able to construct an initial dose distribution model and obtain the standard dose distribution model by correcting the initial dose distribution model with the correction model Because the standard dose distribution model is obtained by correcting the constructed initial dose distribution model, the mapping relationship between the dose distribution data and the density values in the standard dose distribution model is more accurate, which further makes the obtained dose distribution data of each spatial point more accurate.

In some embodiments, the correction component 150 may include multiple correction blocks of various sizes. The correction blocks may be cube correction blocks having a side length of 0.1 mm to 30 mm. The multiple cube correction blocks of various sizes can be spliced to form the correction component 150 of a cuboid shape.

According to the apparatus for detecting the spatial dose distribution of the article in the embodiment of the present disclosure, the result of the detected dose distribution information of the article to be detected can be graphically displayed and output as data. In some embodiments, a suitable application interface may be developed to display an ultra-high-definition three-dimensional image on the display device 140. In the application interface, a fluoroscopy image of an interior of the article to be detected may be viewed from any angle, and fault cross-section information of the interior of the article to be detected may be displayed.

FIG. 17 to FIG. 20 respectively show schematic diagrams of the interface displayed by the display device in the apparatus for detecting the spatial dose distribution of the article according to the embodiments of the present disclosure. FIG. 17 to FIG. 20 respectively show schematic diagrams of the interface when the apparatus is used to detect different types of articles.

Figure 17:
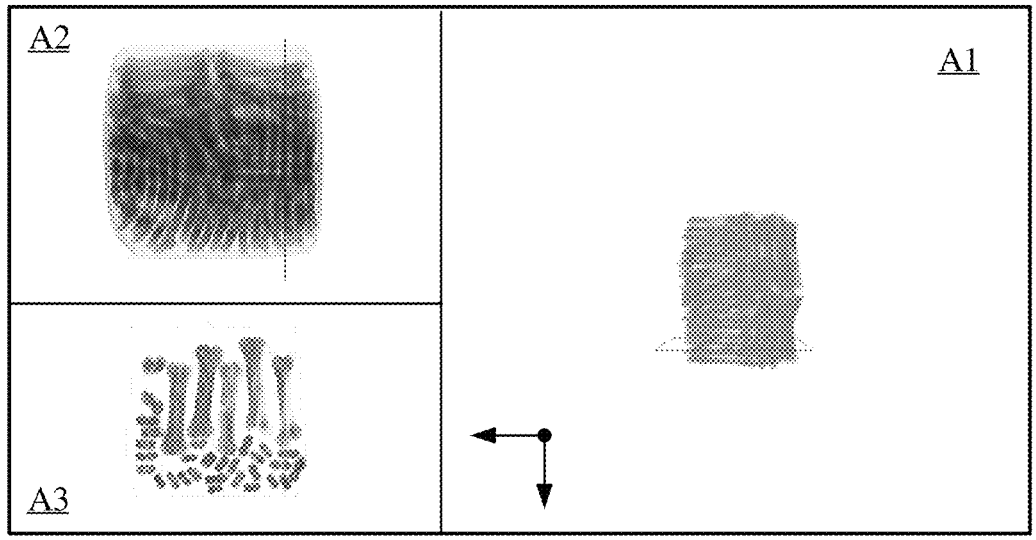
FIG. 17 to FIG. 20 are schematic diagrams showing an interface displayed by a display device in an apparatus for detecting a spatial dose distribution of an article according to an embodiment of the present disclosure.
Figure 18:
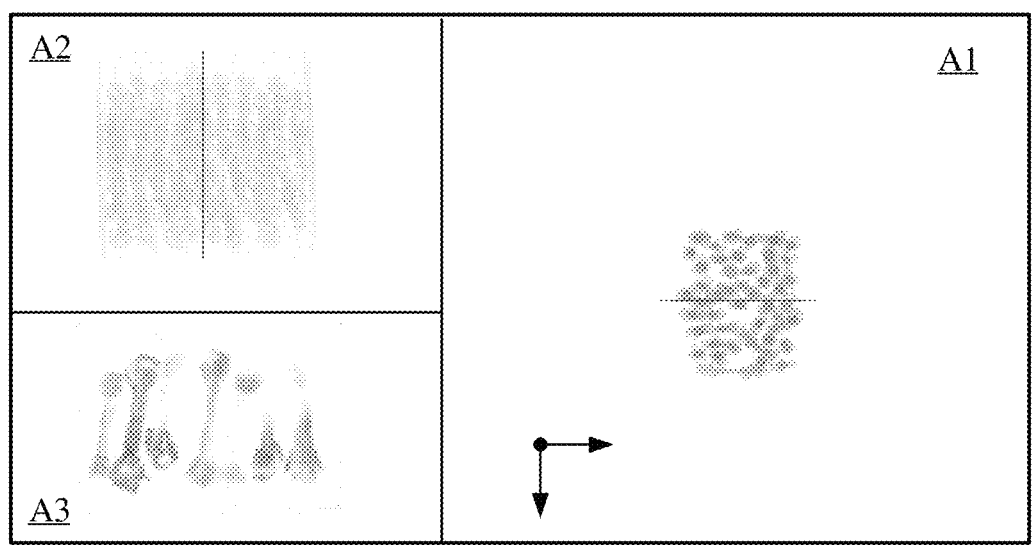
Figure 19:
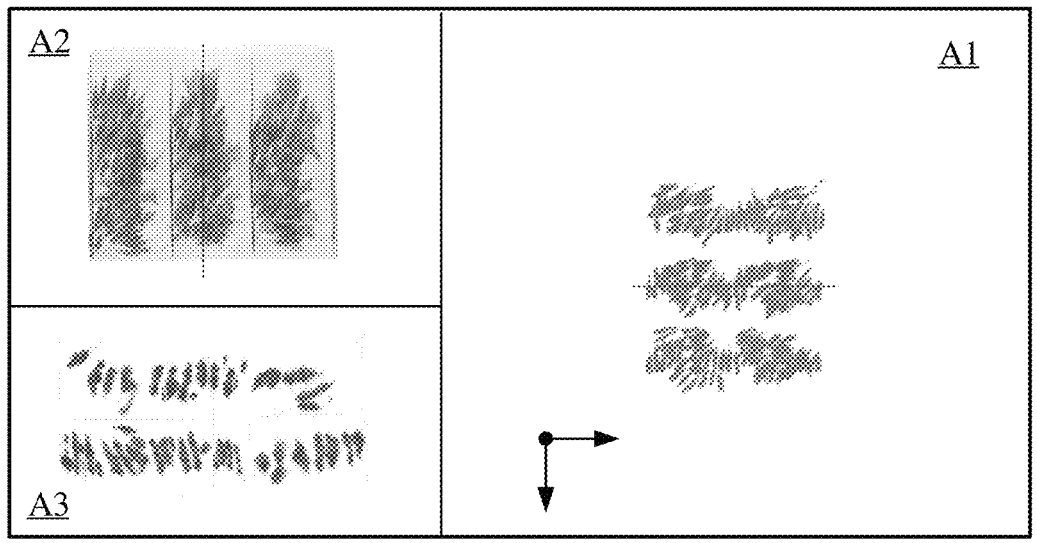
Figure 20:
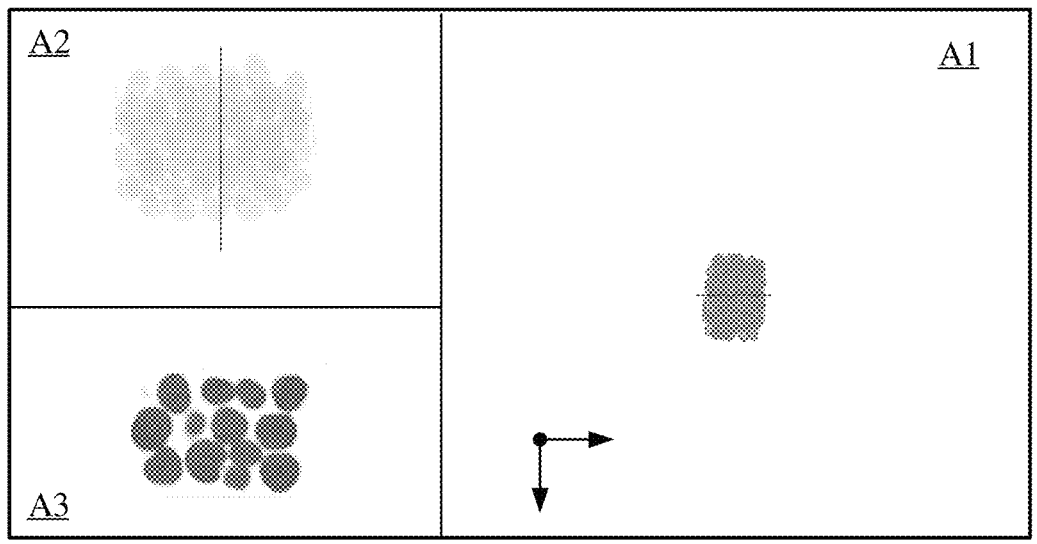

FIG. 17 and FIG. 18 are schematic diagrams of the interface when the apparatus is used to detect pet food, FIG. 19 is a schematic diagram of the interface when the apparatus is used to detect food chicken feet, and FIG. 20 is a schematic diagram of the interface when the apparatus is used to detect fruit cherry. In FIG. 17 to FIG. 20, the interface displayed on the display device 140 may include a plurality of regions, namely a first region A1 located on the right side, a second region A2 located on the upper left side, and a third region A3 located on the lower left side. Among them, the first region A1 may be used to display a stereoscopic image of the article to be detected, the second region A2 may be switched to display a six-view image of the article to be detected, and the third region A3 may be used to display an image of a certain cross-section of the interior of the article to be detected. The straight line in the second region A2 shows the cut position of the cross-section image.

In the interface displayed on the display device 140, the internal structure of the article to be detected and the data corresponding to each spatial point can be viewed at full angle, and a certain cross-section inside can be zoomed in and viewed. FIG. 17 and FIG. 18 respectively show the interface at different angles for the pet food.

In the interface displayed on the display device 140, different penetration thickness intervals may be distinguished by different colors or chromaticities, and the dose distribution data corresponding to any spatial point or area may be displayed by selecting the corresponding point or frame-selecting the corresponding area. The dose distribution information may include the ratio of the maximum dose to the surface dose, the ratio of the minimum dose to the surface dose, and the dose unevenness of the article to be detected and each unit inside. In this way, analysis results and suggested schemes can be provided for the subsequent irradiation processing of the article to be detected. For example, suggestions about whether the article to be detected is suitable for irradiation, a dose distribution level, and the like can be provided.

According to the apparatus for detecting the spatial dose distribution of the article according to the embodiment of the present disclosure, the dose distribution data of each spatial point of the article to be detected may be matched with the stereoscopic fluoroscopy image to obtain a three-dimensional stereoscopic radiation image, and image information of each spatial point of the article to be detected and the dose distribution data may be displayed on the display device 140. In this way, the dose distribution data of each spatial point of the article to be detected may be more intuitive and accurate, which may facilitate a reasonable configuration of various parameters in the irradiation processing. Compared with conventional techniques, the method for detecting the spatial dose distribution of the article may have the advantages of short test cycle, high speed and efficiency, high accuracy of test results, and clear internal conditions of the article, which can greatly improve the operational efficiency at the irradiation processing site.

It is to be understood that the embodiments of the present disclosure are not limited to the specific configurations and processes described above and shown in the drawings. For the purpose of concision, the detailed description of known technique is omitted herein. In the above embodiments, a number of specific steps are described and illustrated as examples. However, the processes of the embodiments of the present disclosure are not limited to the specific steps described and illustrated. A person skilled in the art may make various changes, modifications and additions, or change the order of the steps after understanding the spirit of the present disclosure.

The functional blocks shown in the structural block diagrams described above can be implemented as hardware, software, firmware, or a combination thereof. When implemented in hardware, it may be, for example, an electronic circuit, an application specific integrated circuit (ASIC), appropriate firmware, a plug-in, a function card, and so on. When implemented in software, the elements of the present disclosure may be a program or a code segment that is used to perform the required tasks. The program or the code segment may be stored in a machine-readable medium, or transmitted on a transmission medium or a communication link through a data signal carried in a carrier wave. "Machine-readable medium" may include any medium capable of storing or transmitting information. Examples of the machine-readable medium may include an electronic circuit, a semiconductor memory device, ROM, flash memory, erasable ROM (EROM), a floppy disk, CD-ROM, an optical disk, a hard disk, fiber optic medium, a radio frequency (RF) link, and so on. The code segment can be downloaded via a computer network such as the Internet, an intranet, and so on.

It should also be noted that the exemplary embodiments mentioned in the present disclosure describe some methods or systems based on a series of steps or devices. However, the present disclosure is not limited to the order of the above steps, that is, the steps may be performed in the order mentioned in the embodiments and may also be performed in an order different from the order in the embodiments, or several steps may be performed simultaneously.

The above description is only for illustrating the specific embodiments of the present disclosure. It will be apparent to those skilled in the art that, for the sake of convenience and simplicity of description, specific operating processes of the systems, units and elements described above may be known by referring to corresponding processes in the foregoing method embodiments, and will not be repeated herein. It is to be understood that the scope of the present disclosure is not limited thereto. Within the technical scope of the present disclosure, various modifications or substitutions may be readily apparent to those skilled in the art, and all of the modifications or substitutions are to be included within the scope of the present disclosure.

What is claimed is:

1. A method for detecting a dose distribution of an article, comprising:
   performing a fluoroscopy scanning on the article, to obtain mass data per unit area or unit volume for each point of the article;
   obtaining corresponding dose distribution data based on the mass data per unit area or unit volume and a preset mapping model, wherein the preset mapping model includes a mapping relationship between mass per unit area or unit volume and the dose distribution of the article under irradiation of a preset amount of energy;
   matching the dose distribution data with a fluoroscopy image of the article; and
   generating a radiation image of the article for displaying the dose distribution data matched with the fluoroscopy image of the article.

2. The method of claim 1, wherein the radiation image is a planar image and the method further comprises:
   obtaining, when the article is scanned by X-rays, mass thickness data of the article under irradiation energy corresponding to the X-rays;
   classifying mass thickness values in the mass thickness data according to a mass thickness classification condition corresponding to the article, wherein the mass thickness classification condition is determined based on mapping relationship data between the mass thickness values and electron beam irradiation dose distribution data corresponding to the article; and
   generating, based on each mass thickness value, a classification of the mass thickness value and the electron beam irradiation dose distribution data, the radiation image for displaying the mass thickness values and the electron beam irradiation dose distribution data of the article.

3. The method of claim 2, wherein the determination of the mass thickness classification condition comprises:
   determining a dose unevenness value corresponding to each mass thickness value based on the mapping relationship data;
   creating a mapping relationship curve based on each mass thickness value and the dose unevenness value corresponding to the mass thickness value; and
   determining multiple critical points in the mapping relationship curve, and classifying the mass thickness values into multiple classes based on the multiple critical points.

4. The method of claim 3, wherein the determining multiple critical points in the mapping relationship curve comprises:
   determining, when the article is subjected to single-sided irradiation, the multiple critical points in the mapping relationship curve based on a preset maximum unevenness; and
   determining, when the article is subjected to double-sided irradiation, the multiple critical points in the mapping relationship curve based on the preset maximum unevenness and a valley value of the mapping relationship curve.

5. The method of claim 2, wherein the generating, based on each mass thickness value, a classification of the mass thickness value and the electron beam irradiation dose distribution data, the radiation image for displaying the mass thickness values and the electron beam irradiation dose distribution data of the article comprises:
   assigning a display pattern corresponding to each mass thickness value based on each mass thickness value and the classification of the mass thickness value; and
   generating the radiation image of the article, based on the display pattern corresponding to each mass thickness value.

6. The method of claim 5, wherein the generating, based on each mass thickness value, a classification of the mass thickness value and the electron beam irradiation dose distribution data, the radiation image for displaying the mass thickness values and the electron beam irradiation dose distribution data of the article further comprises:

obtaining a mass thickness value corresponding to a target pixel point or a target area in the radiation image;

querying, from the mapping relationship data, the electron beam irradiation dose distribution data corresponding to the mass thickness value of the target pixel point or the target area; and displaying the electron beam irradiation dose distribution data in the target area.

7. The method of claim 6, wherein the generating, based on each mass thickness value, a classification of the mass thickness value and the electron beam irradiation dose distribution data, the radiation image for displaying the mass thickness values and the electron beam irradiation dose distribution data of the article further comprises:

determining a dose unevenness value corresponding to the target pixel point or the target area, based on the electron beam irradiation dose distribution data corresponding to the mass thickness value of the target pixel point or the target area;

determining irradiation effect based on a comparison result between the dose unevenness value and a preset maximum unevenness; and displaying the dose unevenness value and the irradiation effect in the target area.

8. The method of claim 1, wherein the radiation image is a stereoscopic image and the method further comprises:

constructing a standard dose distribution model, wherein the standard dose distribution model includes a standard mapping relationship between the dose distribution data and density values of the article under the irradiation of the preset amount of energy;

performing the fluoroscopy scanning on the article, to obtain a stereoscopic fluoroscopy image of the article and a detected density value of each spatial point of the article;

obtaining dose distribution data of each spatial point of the article, based on the detected density value of each spatial point of the article and the standard mapping relationship in the standard dose distribution model; and matching and displaying the dose distribution data of each spatial point of the article with the stereoscopic fluoroscopy image.

9. The method of claim 8, wherein the constructing a standard dose distribution model comprises:

constructing an initial dose distribution model, wherein the initial dose distribution model includes a theoretical mapping relationship between the dose distribution data and theoretical density values of the article under the irradiation of the preset amount of energy;

obtaining a correction model; and obtaining the standard dose distribution model by correcting the initial dose distribution model with the correction model.

10. The method of claim 9, wherein the obtaining a correction model comprises:

providing a correction component matching the article, wherein the correction component includes multiple correction blocks of various sizes;

performing a fluoroscopy scanning on the correction component to obtain theoretical density values of the correction component;

measuring masses and sizes of the multiple correction blocks to calculate multiple real density values corresponding to the multiple correction blocks; and fitting the multiple real density values with the theoretical density values to obtain the correction model.

11. The method of claim 10, wherein the fitting the multiple actual density values with the theoretical density values to obtain the correction model comprises performing a polynomial fitting between the multiple real density values and the theoretical density values.

12. The method of claim 10, wherein the multiple correction blocks are multiple cube correction blocks having a side length of 0.1 mm to 30 mm, and the multiple cube correction blocks of various sizes are to be spliced to form the correction component of a cuboid shape.

13. The method of claim 8, wherein the dose distribution data comprises at least one of:

ratio data of a maximum dose to a surface dose;

ratio data of a minimum dose to the surface dose; and dose unevenness data.

14. The method of claim 8, wherein the preset amount of energy is in a range of 1 MeV to 20 MeV.

15. An apparatus for detecting a dose distribution of an article, comprising:

a fluoroscopy unit configured to perform a fluoroscopy scanning on the article, to obtain mass data per unit area or unit volume for each point of the article;

a data processing unit configured to obtain corresponding dose distribution data based on the mass data per unit area or unit volume and a preset mapping model, wherein the preset mapping model includes a mapping relationship between mass per unit area or unit volume and the dose distribution of the article under irradiation of a preset amount of energy; and an image processing unit configured to match the dose distribution data with a fluoroscopy image of the article, and generate a radiation image of the article for displaying the dose distribution data matched with the fluoroscopy image of the article.

16. The apparatus of claim 15, wherein:

the fluoroscopy unit includes a data obtaining unit configured to obtain, when the article is scanned by X-rays, mass thickness data of the article under irradiation energy corresponding to the X-rays;

the data processing unit includes a data classification unit configured to classify mass thickness values in the mass thickness data according to a mass thickness classification condition corresponding to the article, wherein the mass thickness classification condition is determined based on mapping relationship data between the mass thickness values and electron beam irradiation dose distribution data corresponding to the article; and the image processing unit includes an image generation unit configured to generate, based on each mass thickness value, a classification of the mass thickness value and the electron beam irradiation dose distribution data, the radiation image for displaying the mass thickness values and the electron beam irradiation dose distribution data of the article.

17. The apparatus of claim 15, further comprising:

a model processing device configured to construct a standard dose distribution model, wherein the standard dose distribution model includes a standard mapping relationship between the dose distribution data and density values of the article under the irradiation of the preset amount of energy, wherein:

the fluoroscopy unit includes a stereoscopic fluoroscopy device configured to perform the fluoroscopy scanning on the article, to obtain a stereoscopic fluoroscopy image of the article and a detected density value of each spatial point of the article;

the data processing unit includes a calculation device connected to the model processing device and the stereoscopic fluoroscopy device and configured to obtain the dose distribution data of each spatial point of the article, based on the detected density value of each spatial point of the article and the standard mapping relationship in the standard dose distribution model; and the image processing unit includes a display device connected to the calculation device and configured to match and display the dose distribution data of each spatial point of the article with the stereoscopic fluoroscopy image.

18. The apparatus of claim 17, further comprising:

a correction component configured to be subjected to a fluoroscopy scanning by the stereoscopic fluoroscopy unit to obtain a correction model, wherein the model processing device is to construct an initial dose distribution model and obtain the standard dose distribution model by correcting the initial dose distribution model with the correction model.

19. The apparatus of claim 18, wherein the correction component includes multiple correction blocks of various sizes, the multiple correction blocks are multiple cube correction blocks having a side length of 0.1 mm to 30 mm, and the multiple cube correction blocks of various sizes are to be spliced to form the correction component of a cuboid shape.

* * * * *